United States Patent [19]

Cooper et al.

[11] Patent Number: 4,729,657
[45] Date of Patent: Mar. 8, 1988

[54] METHOD OF CALIBRATING REFLECTANCE MEASURING DEVICES

[75] Inventors: David M. Cooper, Duluth, Ga.; Ralph S. Hernicz, Elk Grove Village, Ill.

[73] Assignee: Miles Laboratories, Inc., Elkhart, Ind.

[21] Appl. No.: 877,169

[22] Filed: Jun. 23, 1986

[51] Int. Cl.$^4$ ............................................. G01J 3/02
[52] U.S. Cl. ...................................... 356/319; 356/446
[58] Field of Search ............... 356/300, 319, 320, 323, 356/325, 326, 328, 418, 445-448, 243; 364/498

[56] References Cited

U.S. PATENT DOCUMENTS

| | | | |
|---|---|---|---|
| 3,828,173 | 8/1974 | Knepler | 356/418 |
| 3,874,799 | 4/1975 | Isaacs et al. | 356/323 |
| 4,526,470 | 7/1985 | Kaye | 356/319 |

Primary Examiner—F. L. Evans
Attorney, Agent, or Firm—Roger N. Coe

[57] ABSTRACT

A method of calibrating reflectance measuring devices, such as spectrophotometers, that incorporate automatic gain or sensitivity setting capability. According to the method, offset reflectance and reflectance of a secondary reflectance standard for several wavelengths are calculated and stored in a memory of a reflectance measuring device. A secondary standard is mounted in the reflectance measuring device and reflectances at a selected wavelengths from the secondary standard are read prior to measurement of the reflectance of the test sample. The stored offset reflectance and secondary reflectance for the operational wavelength are used to calculate true reflectance of the test sample.

4 Claims, 2 Drawing Figures

METHOD OF CALIBRATING REFLECTANCE MEASURING DEVICES

FIELD OF THE INVENTION

The present invention relates to a new and improved method of calibrating reflectance measuring devices and to a method of measuring light reflectance from a test specimen. More particularly, the invention is directed to a method of calibration of, measurement and measurement correction of light reflectance in a light reflectance device that incorporates an automatic gain or sensitivity setting. Light reflectance measurement from a single, secondary reflectance standard, prior to measurement of reflectance from a test sample, enables the calculation of accurate true reflectances from the test specimen reflectance measurement.

BACKGROUND OF THE INVENTION AND PRIOR ART

Reflectance ratio is the ratio of the intensity of light reflected from a sample to the intensity of light incident on the sample. It is relatively easy to measure the intensity of light reflected from a sample, however, measuring the light incident on the sample is more difficult. Incident light has been measured by placing a primary reflectance standard in a readhead of a spectrophotometer and, by knowing the true reflectance at the operational wavelength of the device, the incident light can be back-calculated from the detected deflectance. Reflectance of the test sample then is determined from the intensity of light reflected from the test sample divided by the intensity of light reflected from the primary reflectance standard multiplied by the known reflectance of the reflectance standard. This technique assumes that there is no stray light within the reflectance measuring device, but this assumption is wrong and leads to significant measurement errors.

To calibrate reflectance measuring devices, such as spectrophotometers, it is customary to establish 100% and 0% reflectance values. To establish these reflectance values, a measurement relative to some standard must be made. The 0% reflectance value has been difficult to obtain, and many procedures and devices operate on the assumption that 0% reflectance is the value measured with the device turned off. The resulting 0% reflectance value is not correct since it is very difficult to impossible to eliminate stray light.

In the prior art, recalibration using a primary reflectance standard must be performed before each measurement and the instrument sensitivity or gain must be reset. Under these conditions, each measurement and reading is dependent on the sensitivity or gain set of the device. The necessity for the user to place a primary reflectance standard into the device prior to each measurement to reset the instrument sensitivity decreases the utility of the device and increases the cost of use. Further, each reflectance measuring device must be made to close tolerances to insure that the stray light for each device is the same. This requires the maintenance of costly and difficult manufacturing tolerances and strict quality control standards. Another disadvantage with these devices is a need for frequent device recalibration due to constant sensitivity changes.

One approach to calibrating spectrophotometers is disclosed in U.S. Pat. No. 4,029,419. In this system, the spectrophotometer is calibrated by using a secondary white standard calibrated against a primary white standard, a black standard to compersate for dark current and internal reflectance from a pressure plate, and a mirror to obtain internal wall reflectance used in a correction factor. Although this approach does not assume that the stray light is zero, for each use of the spectrophotometer two samples must be read and the instrument recalibrated.

A process of compensating for radiation variances in a spectrophotometer light source is disclosed in U.S. Pat. No. 3,245,305. The spectrophotometer described in this patent employs two light sources and means for sensing the relative intensities of the radiation from the two sources. The device of U.S. Pat. No. 3,245,305 also includes means for altering the intensity of the radiation from one light source. Additional apparatus is provided to be responsive to the sensing apparatus for automatically changing the intensity of the radiation from one light source to keep the ratio of the intensity of the two light sources constant. This device does not measure the incident light directly. Further, the requirement of a second light source and the attendant electronics increases the complexity and cost of the device and its use.

U.S. Pat. No. 3,646,331 discloses a method and apparatus for correcting radiation measurment errors in a spectrophotometer by digitizing the output of a 100% line input at selected discrete wavelengths. A factor, called a M factor, is computed from the output at each discrete wavelength such that the digitized output multiplied by the M factor will give a corrected 100% output at each wavelength. These M factors are each stored, and during a sample measurement by the spectrophctometer, each of the stored M factors is synchronously applied to multiply the input signal derived from the signal, thereby generating a corrected output. This apparatus and method completely neglects the 0% reflectance value, whereby a significant, inherent error is introduced into the apparatus and method.

U.S. Pat. No. 4,310,243 discloses a spectrophotometer and a method of simultaneously compensating for the dark current of a photomultiplier tube and the offset of an operational amplifier in the spectrophotometer, so that the output voltage of the operational amplifier is zero volts under dark conditions. Although this patent discloses a technique for compensating for the dark signal of a detector, it does not account for stray light.

SUMMARY OF THE INVENTION

An object of the present invention is to provide a new and improved method for calibrating reflectance measuring devices.

Another object of the present invention is to provide a new and improved method of measuring light reflectance from a test sample.

Another object of the present invention is to provide a new and improved method for calibrating reflectance measuring devices that incorporate automatic gain or sensitivity setting capability or are otherwise subject to significant sensitivity changes due to time, use and environmental conditions.

A further object of the present invention is to provide a new and improved method for calibrating reflectance measuring devices that minimizes error due to stray light.

A still further object of the present invention is to provide a new and improved method for calibrating a reflectance measuring device that minimizes the time needed for recalibration.

Another object of the present invention is to provide a new and improved method of calibrating a reflectance measuring device to correct a detected value without recalibrating the device prior to each measurement.

A further object of the present invention is to provide a new and improved method for calibrating a reflectance measuring device that calculates stray light and is independent of the gain set of the device.

Briefly, the present invention is directed to a new and improved method of calibrating reflectance measuring instruments, such as spectrophotometers, and to a method of measuring light reflectance from a test sample. In accordance with one important feature of the present invention, the method of the present invention is particularly useful for reflectometers that incorporate an automatic gain or sensitivity setting or are otherwise subject to significant sensitivity changes due to time, use and environmental conditions. A significant problem in reflectance measuring instruments is the need to constantly recalibrate the instrument due to sensitivity changes. If the instrument is used at several wavelengths and sensitivities vary often, recalibration can be time consuming, and the utility of the instrument ultimately suffers. In the past, measured reflectance has been dependent on the gain set of the instrument. For example, over the life of these instruments, the light source decays and the electronics change. To compensate for these fluctuations, and to keep the light reflected off the sample being measured high thereby providing maximum resolution, the gain is reset prior to each measurement.

Prior art instruments also fail to consider the affect of stray light on the measurements. In spectrophotometry, for example, 100% and 0% reflectance values must be established for correct readings from the instrument. The 0% value is impossible or very difficult to determine due to stray light inherent in all instruments. In the past, stray light has been ignored or assumed to be zero resulting in a significant error in the measurements.

The present invention provides a method to avoid dependence of reflectance measurements on spectrophotometer sensitivity or gain setting and to minimize the error by accurate detection or measurement of stray light. The present invention is directed to a calibration process or method wherein the reflectance of a single, secondary reflectance standard disposed within the readhead is measured just prior to measurement of an unknown test specimen. A set of two coefficients, determined at each operational wavelength of the reflectance measuring device, is used to calculate reflectance of the unknown test specimen. A reflectance standard installation or recalibration process, using a set of at least two, and generally three to five, primary reflectance calibration standards is used to determine and store the coefficients. The set of primary reflectance standards provides the final calibration of the instrument. The single secondary reflectance standard disposed within the readhead achieves quick, short-term calibration of the instrument.

BRIEF DESCRIPTION OF THE DRAWING

The above and other objects and advantages of the present invention will become apparent from the following detailed description of a preferred embodiment of the invention illustrated in the accompanying drawing wherein.

DESCRIPTION OF THE PREFERRED EMBODIMENTS

Figure 1:
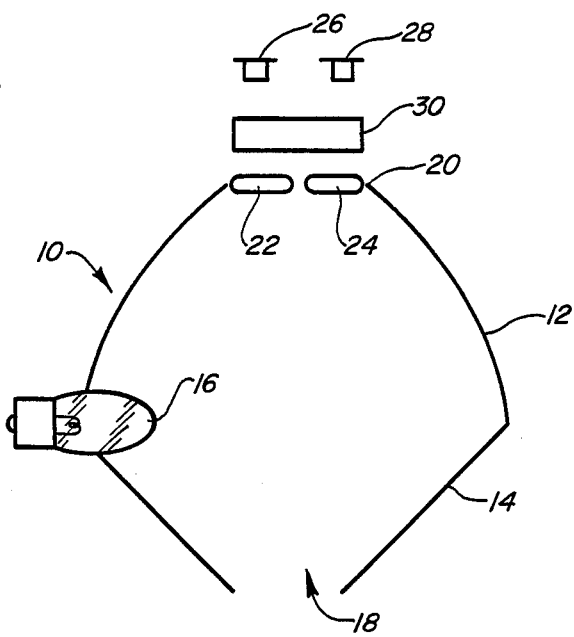
FIG. 1 is a schematic illustration of a readhead for a reflectance measuring instrument such as a spectrophotometer of the type that may be calibrated and used for reflectance measurements in accordance with the principles of the present invention.

Reflectance measuring instruments, such as spectrophotometers, are used to measure reflectance from samples such as, for example, reagent strips. For reagent strip samples, the instrument reading can be, for example, a measure of light reflectance from one or more constituents in a blood sample, such as glucose. The spectrophotometer is an instrument designed to measure reflectance at a selected wavelength corresponding to a specific color.

In the past, the measurements from reflectance instruments have been dependent on the device sensitivity or gain set of the instrument necessitating recalibration prior to each measurement. Usually, recalibration was accomplished, rather crudely, by ignoring the existence of stray light. This failure to compensate for stray light results in significant errors in reflectance measurements.

The present invention is directed to a method of calibrating reflectance measuring devices, such as spectrophotometers, resulting in measurements that are independent of device sensitivity or gain set of the instrument and minimizing the error due to the affect of stray light within the readhead of the device. In accordance with an important feature of the present invention, a secondary reflectance standard is disposed within a sample aperture of the readhead of the reflectance measuring apparatus to obtain a secondary reflectance measurement, while the sample also is disposed near or within the readhead. In accordance with an important feature of the present invention, calibration constants for stray light ($p_o$) and a secondary reflectance standard ($p_c$) are determined for each operational wavelength of the instrument and stored in the instrument's memory. Accordingly, in accordance with an important feature of the present invention, once these constants are stored, the instrument need not be recalibrated prior to each test specimen measurement since the true reflectance of a test specimen ($p_s$) can be calculated from the measured reflectance ($r_s$) without being affected by instrument sensitivity or gain. Accordingly, in accordance with an important feature of the process of the present invention, primary reflectance standards are no longer required to calibrate the reflectance instrument.

A reflectance measuring device produces a numerical output reading ($r_s$) that is proportional to the true sample reflectance ($p_s$) as viewed by the readhead. This relationship is as follows:

$$r_s = K(p_s + p_o). \quad (1)$$

In this equation, K is a scaling factor that includes instrument sensitivity or gain. K can be held constant for short periods, typically minutes, but often has long-term variation due to design, ambient conditions, or use. $p_o$ accounts for the affects of stray light, which afflict all reflectance measuring instruments to some degree. Stray light, which cannot be removed by simple dark reading subtraction, affects the output reading ($r_s$) the same as if a small additional offset reflectance, $p_o$, were present in the readhead along with the sample.

During calibration of the instrument several primary reflectance standards with different known reflectances are read in the instrument. A data set of the form:

$$(p_1, r_1), (p_2, r_2) \ldots (p_n, r_n)$$

results at each wavelength of operation of the instrument. In gathering this data, the primary reflectance standards can be constructed, for example, by loading Plexiglas with varying mixtures of $BaSO_4$ and carbon black. The samples then can be measured on a Cary 17 Spectrophotometer. These measurements are traceable to the National Bureau of Standards.

Figure 2:
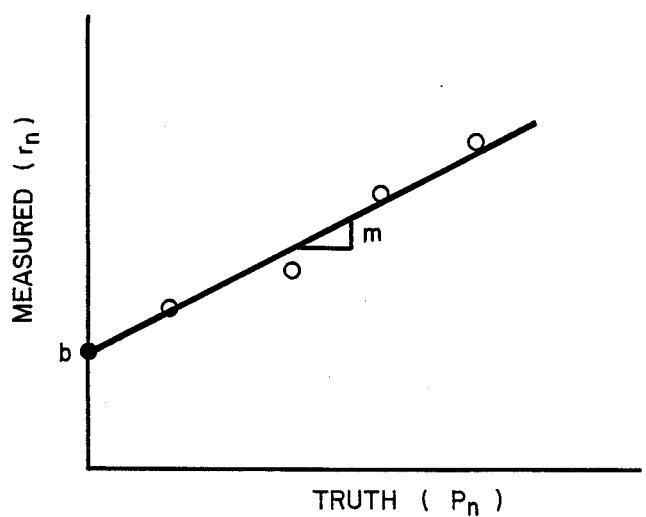
FIG. 2 is a graphic illustration of a least-squares linear regression line plotted through data collected by reading reflectance from a plurality of primary reflectance standards each with a known reflectance.

The data from measurements of the primary standards is plotted on a graph as in FIG. 2 for truth or actual values ($p_1, p_2 \ldots p_n$) versus measured values ($r_1, r_2, \ldots r_n$). A least-squares linear regression line of the form:

$$r_n = m\,p_n + b \qquad (2)$$
$$= m(p_n + b/m)$$

then is calculated for the data from each wavelength of operation where m is the slope and b is the vertical axis intercept for the line in FIG. 2. K, m and b may be different at each wavelength of operation.

In comparing equations (1) and (2) it is noted that:

$$m = k$$

and $$b/m = p_o.$$

The reflectance of the secondary reflectance standard ($p_c$) also can be calculated from equation (2):

$$r_c = m\,p_c + b$$

and $$p_c = (r_c - b)/m \qquad (3)$$

In this manner, b, m, $p_c$ and $p_o$ are calculated for each wavelength of instrument operation. The constants $p_c$ and $p_o$ for each wavelength are stored in the memory of the reflectance measuring instrument for future use.

In accordance with an important feature of the present invention, $p_s$, true sample reflectance, is computed independent of K by reading the light reflectance from a stable, relatively highly reflective secondary standard just prior to the measurement of each unknown test specimen. When the secondary standard reflectance ($p_c$) is read:

$$r_c = K(p_c + p_o)$$

or, solving for K;

$$K = r_c/(p_c + p_o) \qquad (4)$$

where $p_c$ is the reflectance (previously calculated and stored) of the secondary standard.

Rearranging equation (1), the following is obtained:

$$p_s = (r_s/K) - p_o. \qquad (5)$$

In order to eliminate K, equation (4) is substituted into equation (5):

$$p_s = (r_s(p_c + p_o)/r_c) - p_o \qquad (6)$$
$$= p_c(r_s/r_c) + p_o(r_s/r_c - 1).$$

The reflectance of an unknown test specimen can be calculated using equation (6) from readings of the sample ($r_s$) and the secondary standard reflectance ($r_c$) and from the appropriate stored values of $p_c$ and $p_o$. This calculation is independent of spectrophotometer sensitivity (part of K) as long as K is stable during the reflectance readings of the secondary standard and the unknown sample.

In equation (6), if the stray light were assumed to be zero as is done in the prior art, $p_o$ would be zero resulting in a potentially significant reflectance error equal to $$p_o(r_s/r_c - 1).$$

This error is greatest at small sample reflectances where $r_s$ is much smaller than $r_c$.

The process as described provides two constants ($p_c$ and $p_o$) that once determined for each wavelength, can be stored in an erasable memory of each instrument. The instruments then can be used to read the reflectance from the secondary standard ($r_c$) followed by a reading of the reflectance from the test specimen ($r_s$). With this information, the electronics of the instrument make the calculation of equation (6) to determine quickly and accurately the true reflectance of the test specimen ($p_s$). This measurement is independent of the gain (K) of the instrument and minimizes the error due to stray light. Independence from the gain allows the instrument to be operated by a lay person, thereby reducing the cost of operation. The minimization of the error due to stray light increases the accuracy of the reading by the instrument thereby improving diagnosis.

To more fully understand the present invention, reference is directed to FIG. 1. In FIG. 1 a readhead is schematically illustrated and generally designated by the reference numeral 10. Readhead 10 is, for example, of the type used in spectrophotometers and is described more fully in U.S. patent application Ser. No. 659,416, filed on Oct 10, 1984, now U.S. Pat. No. 4,659,229, assigned to the assignee of the present invention and incorporated by reference. Readhead 10 includes a hemispherical upper wall 12 and a conical lower wall 14. Mounted in the readhead 10 is a broad spectrum light source 16, preferably a Xenon flash lamp. A sample aperture 18 is provided in the bottom of readhead 10 for separate positioning of the secondary reflectance standard (not shown) and a test specimen (not shown) that is to be measured. A second aperture 20 is provided in the upper end of readhead 10 with first and second lenses 22 and 24 positioned in second aperture 20. First lens 22 is focused on the test specimen and second lens 24 is focused on the inside wall of readhead 10.

In accordance with the present invention, the secondary standard first is disposed within the aperture 18 in a predetermined position within the readhead 10 with the test specimen also within the readhead 10 in a predetermined p.osition to obtain a secondary standard reflectance measurement $r_c$. Shortly thereafter, the test specimen is disposed within the aperture 18 of readhead 10 and the secondary standard disposed in a predetermined position within the readhead 10 to obtain a test specimen reflectance measurement $r_s$. During these measurements, light from light source 16 reflects from the inside of readhead 10 and impinges on the secondary reflectance standard and test sample from all directions. The light reflected from the secondary reflectance standard and test sample is focused by lens 22 onto a first detector or photodiode 26. Reflectance detected by photodiode 26 is measured by the instrument in accordance with known electronics to provide reflectance readings ($r_s$ and $r_c$) proportional, respectively, to the true reflectance of the test specimen ($p_s$) and the true reflectance of the secondary standard ($p_c$). The second lens 24 focuses light reflected from the inside of readhead 10 onto a second detector or photodiode 28. The reading obtained from the second detector 28 is used to correct the reflectances $r_s$ and $r_c$ measured at photodiode 26 to compensate for short term variations in light from light source 16. An interference filter 30 is disposed between the lenses 22 and 24 and the detectors 26 and 28 to allow only light of preselected wavelength to reach the detectors 26 and 28. A reflectance measuring instrument, such as a spectrophotometer (not shown) including the readhead 10 also includes electronics and a memory as well known in the art capable of performing the calculations described herein.

The instrument first reads a reflectance at a preselected operational wavelength from the secondary standard ($r_c$) allowing the instrument to compensate for long term drifts in the instrument by automatically changing the sensitivity or gain. The test specimen then is positioned in aperture 18 and the secondary standard repositioned to another preselected position within the readhead 10 for a measurement of the reflectance from the test sample ($r_s$). The process of the present invention enables much faster and more accurate measurements than prior art methods since it is not necessary to calibrate the instrument prior to each measurement or reading.

The apparatus and method of the present invention also are convenient to the customer since a lay person easily can use the instrument. The costs of purchasing the apparatus of the present invention to obtain reflectance measurements are much lower than the prior art since primary standards are not required and need not be maintained. The present invention also is more accurate than the prior art processes since stray light is calculated and incorporated into the reflectance measurement calculations.

Many modifications and variations of the present invention are possible in light of the above teachings. Thus, it is to be understood that, within the scope of the appended claims, the invention can be practiced other than as specifically described in the above description.

What is claimed and desired to be secured by Letters Patent of the United States is:

1. A method of calibrating a spectrophotometer for measuring the reflectance of a test sample, said spectrophotometer including a readhead, a broad spectrum light source mounted in said readhead, a first sample aperture, a second aperture, at least one lens in said second aperture, at least one detector for collecting reflected light whereby said detector provides an output signal proportional to the intensity of collected reflected light, a secondary reflectance standard in said readhead and a memory, the method comprising:

detecting the amount of light reflected from at least two primary reflectance standards with different known reflectances for a plurality of wavelengths of operation of said spectrophotometer;

calculating a least-squares linear regression line for said known reflectances and the output signals for said primary reflectance standards at a plurality of wavelengths of operation;

calculating an offset reflectance for stray light for a plurality of wavelengths using the slope and intercept of said least-squares linear regression lines;

detecting for said plurality of wavelengths the amount of light reflected from a secondary reflectance standard with a known reflectance;

calculating the secondary standard reflectance for said plurality of wavelengths of spectrophotometer operation using the slope and intercept of said least-squares linear regression lines; and storing said offset reflectance and said secondary standard reflectance for said plurality of wavelengths in said memory.

2. The method of claim 1 further comprising:

placing a sample of unknown reflectance adjacent said first sample aperture;

measuring the amount of light reflected from said secondary reflectance standard;

measuring the amount of light reflected from said sample; and calculating the reflectance of said sample using the stored reflectance measurements.

3. A method for calculating true sample reflectance for a sample as viewed by a readhead of a spectrophotometer that incorporates automatic gain or sensitivity setting capability, the steps comprising:

measuring the amount of reflectance of at least two primary reflectance standards having known reflectances for each wavelength of operation of said spectrophotometer;

compiling data including the true reflectance and measured reflectance for each of said primary reflectance standards at each said wavelength;

calculating a least-squares regression line for each said wavelength through said data;

determining the slope m and intercept b for each least-squares regression line;

calculating a stray light constant $p_o$ for each wavelength according to:

$$p_o = b/m;$$

measuring the amount of reflectance $r_c$ of a secondary standard reflectance having a known reflectance for a plurality of wavelengths of operation of said spectrophotometer;

calculating the secondary standard reflectance $p_c$ according to:

$$p_c = (r_c - b)/m;$$

measuring the amount of reflectance $r_s$ of said sample; and calculating the true sample reflectance $p_s$ according to:

$$p_s = p_c(r_s/r_c) + p_o(r_s/r_c - 1).$$

4. A method of measuring the reflectance of a sample using a spectrophotometer, comprising:

storing a value for offset reflectance at different wavelengths;
storing a value for secondary standard reflectance at different wavelengths;
exposing a secondary reflectance standard to light;
measuring the amount of light reflected from said secondary reflectance standard;
exposing said sample to said light;
measuring the amount of light reflected from said sample; and
calculating true sample reflectance using the ratio of the measured amount of light reflected from the sample and from said secondary reflectance standard and the stored values for offset reflectance and the stored secondary standard reflectance.

* * * * *